United States Patent
Remme

(10) Patent No.: US 11,559,210 B2
(45) Date of Patent: Jan. 24, 2023

(54) METHODS AND APPARATUS TO ESTIMATE VENTRICULAR PRESSURE

(71) Applicant: Cardiaccs AS, Oslo (NO)

(72) Inventor: Espen Wattenberg Remme, Oslo (NO)

(73) Assignee: Cardiaccs AS, Oslo (NO)

( * ) Notice: Subject to any disclaimer, the term of this patent is extended or adjusted under 35 U.S.C. 154(b) by 323 days.

(21) Appl. No.: 16/639,912

(22) PCT Filed: Aug. 16, 2018

(86) PCT No.: PCT/IB2018/056192
§ 371 (c)(1),
(2) Date: Feb. 18, 2020

(87) PCT Pub. No.: WO2019/035052
PCT Pub. Date: Feb. 21, 2019

(65) Prior Publication Data
US 2020/0288990 A1    Sep. 17, 2020

(30) Foreign Application Priority Data

Aug. 17, 2017    (GB) ..................................... 1713215

(51) Int. Cl.
*A61B 5/02*    (2006.01)
*A61B 5/00*    (2006.01)
(Continued)

(52) U.S. Cl.
CPC ........ *A61B 5/02028* (2013.01); *A61B 5/0031* (2013.01); *A61B 5/0215* (2013.01);
(Continued)

(58) Field of Classification Search
None
See application file for complete search history.

(56) References Cited

U.S. PATENT DOCUMENTS

| | | | |
|---|---|---|---|
| 7,513,864 B2 | 4/2009 | Kantrowitz et al. | |
| 2003/0074029 A1* | 4/2003 | Deno ................. | A61N 1/36564 607/23 |

(Continued)

FOREIGN PATENT DOCUMENTS

| | | |
|---|---|---|
| JP | 2009285512 A | 12/2009 |
| JP | 2010524564 A | 7/2010 |

(Continued)

OTHER PUBLICATIONS

International Search Report dated Feb. 10, 2018 for Appl. No. PCT/IB2018/056192, 6 pages.

(Continued)

*Primary Examiner* — John F Mortell
(74) *Attorney, Agent, or Firm* — Sterne, Kessler, Goldstein & Fox P.L.L.C.

(57) ABSTRACT

An approach for determining an estimated pressure curve for the ventricle of the heart, the method comprising: using data from a motion sensor that has been implanted at the heart to determine the timing of heart cycle events; scaling a reference pressure-time curve including timing of reference heart cycle events in order to fit the reference pressure-time curve to the motion sensor data, the scaling comprising scaling the reference curve along the time axis to fit it to the measured timing of the heart cycle events; and thereby obtaining an estimated pressure-time curve in the form of the scaled reference pressure-time curve.

16 Claims, 3 Drawing Sheets

Figure 1:
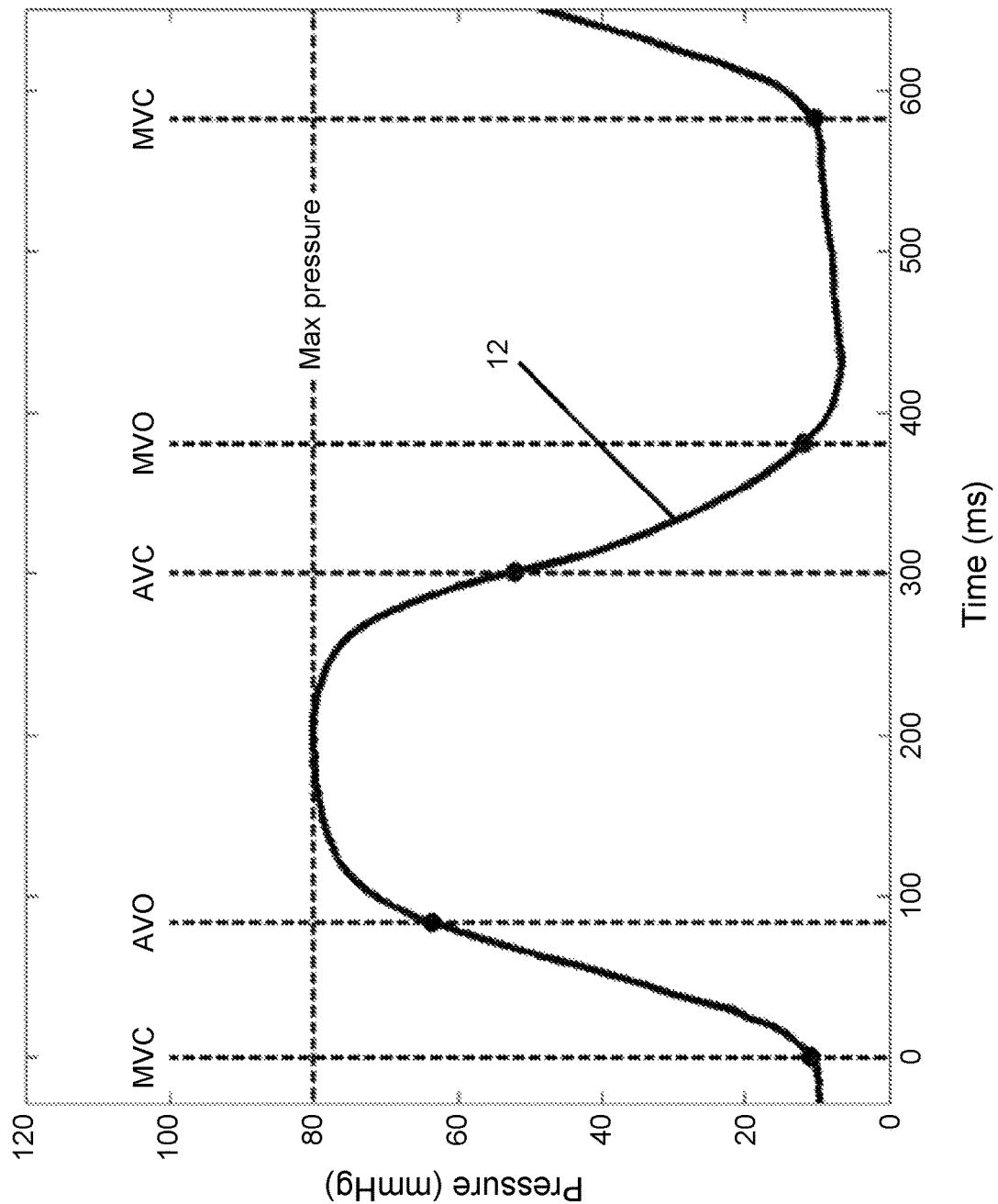

(51) Int. Cl.
*A61B 5/0215* (2006.01)
*A61B 5/11* (2006.01)

(52) U.S. Cl.
CPC ............ *A61B 5/1102* (2013.01); *A61B 5/686* (2013.01); *A61B 5/6869* (2013.01); *A61B 2562/0219* (2013.01)

(56) References Cited

U.S. PATENT DOCUMENTS

| | | | |
|---|---|---|---|
| 2008/0021336 A1 | 1/2008 | Dobak, III | |
| 2008/0281214 A1 | 11/2008 | Elle et al. | |
| 2009/0030471 A1* | 1/2009 | Rousso | A61N 1/36514 607/27 |
| 2013/0053907 A1 | 2/2013 | Kirchner et al. | |
| 2013/0171599 A1* | 7/2013 | Bleich | G16H 20/30 434/247 |
| 2020/0288985 A1* | 9/2020 | Robinson | A61B 5/029 |

FOREIGN PATENT DOCUMENTS

| | | |
|---|---|---|
| WO | WO 2003/061473 A1 | 7/2003 |
| WO | WO 2008/130532 A1 | 10/2008 |
| WO | WO 2009/012030 A1 | 1/2009 |
| WO | WO 2012/055498 A1 | 5/2012 |
| WO | WO 2013/121431 A1 | 8/2013 |

OTHER PUBLICATIONS

Written Opinion dated Feb. 10, 2018 for Appl. No. PCT/IB2018/056192, 8 pages.

Kristoffer Russell et al.: "A novel clinical method for quantification of regional left ventricular pressure-strain loop area: a non-invasive index of myocardial work," European Heart Journal, vol. 33. No. 6, Mar. 1, 2012, pp. 724-733.

Office Action dated Jun. 14, 2022, Japanese Application No. 2020-509017, including English translation, 10 pages.

Per Steinar Halvorsen et al.: "Automatic real-time detection of myocardial ischemia by epicardial accelerometer", The Journal of Thoracic and Cardiovascular Surgery, Apr. 2010, pp. 1026-1032, 7 pages.

* cited by examiner

METHODS AND APPARATUS TO ESTIMATE VENTRICULAR PRESSURE

BACKGROUND OF THE INVENTION

Field of the Invention

The invention relates to a method of determining an estimated pressure curve for a ventricle of the heart as well as to related apparatus and computer programme products.

Background Art

It is often desirable to monitor the function of the heart and/or how the function is altered by medical interventions or devices related to the heart, such as pacemakers and cardiac assist devices. In the prior art various proposals have been made for ways to more effectively monitor a patient in this way in relation to various different parameters of the heart, such as heart rate, displacement, pressure and so on. The relationship between the ventricular pressure and the ventricular motion is very descriptive of the cardiac function and hence can be of particular interest. This relationship can be visualized as a loop by plotting the ventricular displacement on the x-axis and the ventricular pressure on the y-axis as described in relation to the left ventricle by Halvorsen et al. in "Automatic real-time detection of myocardial ischemia by epicardial accelerometer", J. Thorac. Cardiovasc. Surg. 2010 April; 139(4):1026-32. doi: 10.1016/j.jtcvs.2009.05.031. As set out by Halvorsen et al the area of the pressure-displacement loop can be used to detect ischemia in real time with high accuracy. In addition, continuous visualization of this loop may be a valuable tool in perioperative and postoperative patient monitoring of ischemia. However, this method requires knowledge of the ventricular pressure and measuring ventricular pressure requires a pressure catheter to be inserted into the ventricle, which is an invasive procedure associated with stroke risk and hence relatively rarely performed. There is hence a challenge in relation to determining the ventricular pressure.

BRIEF SUMMARY OF THE INVENTION

Embodiments include a method of determining an estimated pressure-time curve for a ventricle of a heart, where the method comprises receiving data from a sensor that has been implanted at the heart, and determining timing of heart cycle events based on the received data. The method further includes scaling a reference pressure-time curve using the determined timing of heart cycle events in order to fit the reference pressure-time curve to the received sensor data, where the scaling comprises scaling the reference pressure-time curve along the time axis to fit to the determined timing of the heart cycle events. The method further includes determining the estimated pressure-time curve based on the scaled reference pressure-time curve.

Other embodiments include a heart monitoring system comprising a motion sensor for implantation at a heart to monitor motion of the heart. The heart monitoring system further comprises a data processing apparatus arranged to receive data from the motion sensor and use the data from the motion sensor or a dedicated sensor for determining a timing of heart cycle events. The data processing apparatus is further arranged to scale a reference pressure-time curve including timing of reference heart valve cycle events in order to fit the reference pressure-time curve to the motion sensor data, the scaling comprising scaling the reference pressure-time curve along the time axis to fit to the measured timing of the heart cycle events. The data processing apparatus is further arranged to obtain an estimated pressure-time curve in the form of the scaled reference pressure-time curve.

Still other embodiments include a computer programme product comprising instructions that, when executed, will configure a data processing apparatus to perform receiving data from a sensor that has been implanted at the heart, and determining a timing of heart cycle events based on the received data. The data processing apparatus is further configured to perform scaling a reference pressure-time curve including using the determined timing of reference heart cycle events in order to fit the reference pressure-time curve to the received sensor data, the scaling comprising scaling the reference pressure-time curve along the time axis to fit to the determined timing of the heart cycle events. The data processing apparatus is further configured to determine the estimated pressure-time curve based on the scaled reference pressure-time curve.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

Figure 2:
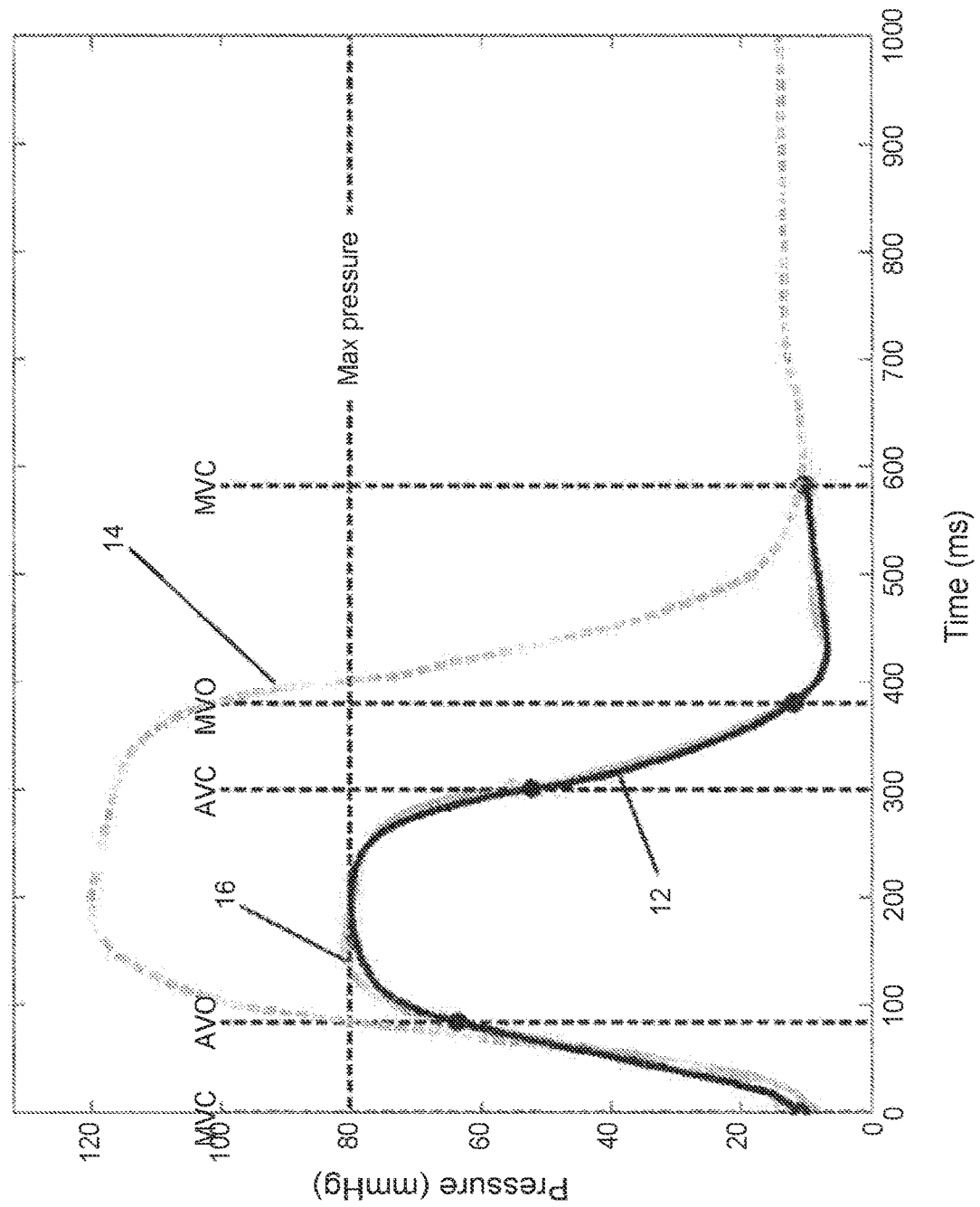
Figure 3:
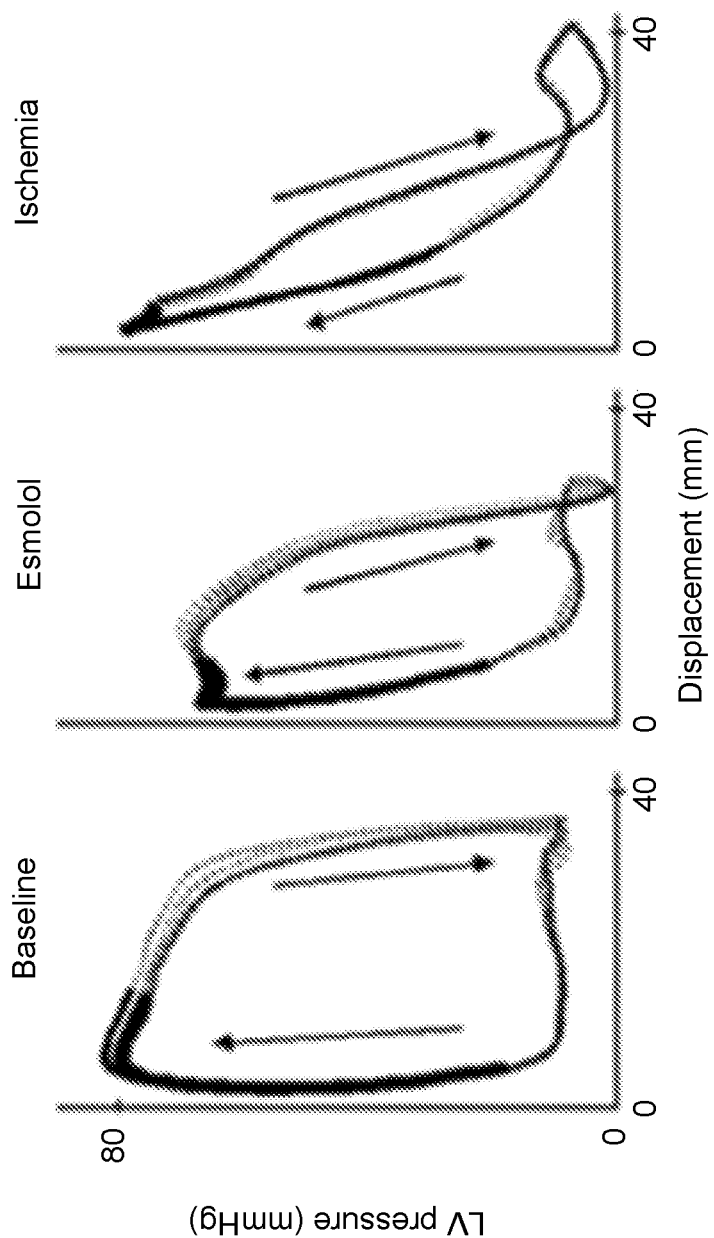

FIG. 1 shows an example left ventricular pressure-time curve along with heart valve opening and closing timing;

FIG. 2 shows the actual left ventricular pressure-time curve of FIG. 1 overlaid with a reference pressure-time curve as well as an estimated pressure-time curve obtained via scaling the reference pressure-time curve to fit measured peak systolic pressure and measured timing for heart valve opening and closing; and FIG. 3 shows how left ventricular pressure-displacement loops vary depending on the condition of the patient.

The present disclosure will be described with reference to the accompanying drawings. In the drawings, like reference numbers indicate identical or functionally similar elements. Additionally, the left most digit(s) of a reference number identifies the drawing in which the reference number first appears.

DETAILED DESCRIPTION OF THE INVENTION

The following Detailed Description refers to accompanying drawings to illustrate exemplary embodiments consistent with the disclosure. References in the Detailed Description to "one exemplary embodiment," "an exemplary embodiment," "an example exemplary embodiment," etc., indicate that the exemplary embodiment described may include a particular feature, structure, or characteristic, but every exemplary embodiment may not necessarily include the particular feature, structure, or characteristic. Moreover, such phrases are not necessarily referring to the same exemplary embodiment. Further, when a particular feature, structure, or characteristic is described in connection with an exemplary embodiment, it is within the knowledge of those skilled in the relevant art(s) to affect such feature, structure, or characteristic in connection with other exemplary embodiments whether or not explicitly described.

The exemplary embodiments described herein are provided for illustrative purposes, and are not limiting. Other exemplary embodiments are possible, and modifications may be made to the exemplary embodiments within the spirit and scope of the disclosure. Therefore, the Detailed Description is not meant to limit the invention. Rather, the scope of the invention is defined only in accordance with the following claims and their equivalents.

The following Detailed Description of the exemplary embodiments will so fully reveal the general nature of the invention that others can, by applying knowledge of those skilled in relevant art(s), readily modify and/or adapt for various applications such exemplary embodiments, without undue experimentation, without departing from the spirit and scope of the disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

In accordance with a proposal by Russell et al. set forth in "A novel clinical method for quantification of regional left ventricular pressure-strain loop area: a non-invasive index of myocardial work.", Eur Heart J. 2012 March; 33(6):724-33. doi:10.1093/eurheartj/ehs016 the left ventricular pressure may be estimated non-invasively. This is done by using a reference pressure-time curve to characterise the shape of the left ventricular pressure as it varies with time and by scaling the reference curve along the pressure axis and the time axis in order to fit it to measured peak systolic pressure and the time of heart valve opening and closing as determined via non-invasive ultrasound measurements. As set out in Russell et al this provided a significant advance in the art since it allows for non-invasive determination of an estimated left ventricular pressure-time curve. There is no need for introducing a pressure catheter into the ventricle. Russell et al. have shown that the estimated pressure-time curve and a corresponding estimated pressure-strain loop correspond well with invasive measurements and with directly measured myocardial work. However, in order to obtain ultrasound measurements, an ultrasound machine has to be brought to the patient or the patient has to come to an ultrasound room. Then the images are obtained. Then they are subsequently analysed manually to determine the valve events. The heart valve timing is hence only valid for the heart beat that was imaged, and in practice this is only easily done when the patient has a detailed examination, or perhaps as the patient is in the hospital before and after a surgery or medical intervention. Thus, in practical terms the timing for the heart valve is determined infrequently and hours apart, i.e. not continuous or in real time. WO 2012/055498 includes similar teaching in the patent literature. In this document examples are provided for determination of parameters concerned with heart function by reference to individual myocardial segments. The method proposed in WO 2012/055498 requires pressure data, and this data is obtained either based on invasive pressure measurement with a pressure sensor placed into the left ventricle or, in preferred embodiments of WO 2012/055498, via non-invasive measurement using ultrasound.

Viewed from a first aspect, the invention provides a method of determining an estimated pressure curve for a ventricle of the heart, the method comprising: using data from a motion sensor that has been implanted at the heart to determine the timing of heart valve events; scaling a reference pressure-time curve including timing of reference heart valve events in order to fit the reference pressure-time curve to the motion sensor data, the scaling comprising scaling the reference curve along the time axis to fit it to the measured timing of the heart valve events; and thereby obtaining an estimated pressure-time curve in the form of the scaled reference pressure-time curve.

This method thus allows for an estimated pressure-time curve for the ventricle to be obtained without the need for a separate measurement of the pressure within the ventricle. As noted above, a similar technique has been described before with reference to using non-invasively measured data to avoid the need for any invasive measurement techniques in the paper by Russell et al. In this earlier work ultrasound is used to determine the timing of the heart valve events. That procedure requires echocardiographic images to be obtained from the patient that are subsequently post-processed for manual determination of the valve events from the images. This procedure is hence performed at few time points. This procedure is replaced by the use of an implanted motion sensor in the method of the first aspect. This allows for continuous or real-time measurements and/or relatively frequent measurements, which is impractical with the use of ultrasound. With such continuous measurements the pressure curve can continually be estimated and re-estimated. The disclosure by Russell et al. strongly teaches that invasive measurements should be avoided and thus teaches against the use of implanted motion sensors. This can in general be a beneficial step. However, the present inventors have made the non-obvious realisation that in some circumstances the requirement for non-invasive measurement in the method proposed by Russell et al. can place undue constraints on the method, and they have also determined that motion sensors placed at the heart can provide increased accuracy and other benefits compared to the prior art method, such as real-time measurements.

Thus, it is proposed to adapt the technique previously disclosed solely for non-invasive measurements in order to use it with data obtained from motion sensors implanted at the heart. It is also proposed to use a similar technique for the left ventricle or the right ventricle. Notably, it is not seen as essential for the present method for the peak pressure to be measured as is proposed in Russell et al. Instead the shape of the estimated pressure curve can be used without the need to know its dimension along the pressure axis. This allows for a more straightforward use of the method with either ventricle, although it is still envisaged that some example implementations will relate to the left ventricle in order to obtain the same advantages and benefits as those taught by Russell et al. In some examples, a measurement of peak pressure is not used and hence the method may comprise scaling the reference pressure curve using the timing of heart valve events without any use of peak pressure to scale the reference pressure curve. However, in other examples, a peak pressure measurement may be used to scale the reference pressure curve along the pressure axis as discussed below, especially in circumstances where a peak pressure measurement is available, such as where the peak systolic pressure of the patient is being measured, for example by arterial pressure or brachial cuff pressure, and the ventricle is the left ventricle.

The method makes use of sensor data that has been obtained from a motion sensor that was previously implanted at the heart. Thus, the method may take place separate to a step of obtaining the data from the motion sensor and it may also take place separate to a step of implanting the motion sensor at the heart. In this way the method can in itself be carried out without any surgical steps and it may make use of data from a motion sensor where this data was obtained for some other procedure as its primary purpose. However, in some examples the method includes the non-surgical step of receiving data from a motion sensor implanted at the heart and the method may include the use of an implanted motion sensor to measure heart movements in order to obtain the required data to determine the timing of the heart valve events.

The motion sensor may already be present at the heart and thus could have been implanted in a separate earlier procedure. However, in some examples the method includes implanting a motion sensor at the heart. The use of a motion sensor implanted at the heart has been proposed for various reasons. For example, EP 1458290 describes a motion sensor in the form of a three-axis accelerometer that is used for registering movements of the surface of the heart. The sensor is designed to be temporarily implanted for monitoring a patient's heart before, during and/or after a surgical operation, for example to monitor for ischemia. U.S. Pat. No. 8,282,568 describes a system that uses data recorded by an accelerometer positioned on an outer surface of the heart for estimating changes in cardiac pumping capacity in response to an intervention. WO 2014/207225 describes the use of an accelerometer implanted at the heart or at a cardiac assist device such as an implanted pump. As set out in in WO 2014/207225 a motion sensor at the heart, such as an accelerometer, can be used to find information about the function of the cardiac assist device as well as information about the function of the heart. It is also known to use a pacemaker device where the pacemaker lead incorporates an accelerometer or other motion sensor to be placed at the heart along with pacemaker electrodes for the purposes of cardiac resynchronisation therapy. The proposed method may make use of such a device, which may be a device previously implanted for cardiac resynchronisation therapy.

The proposed method of determining an estimated pressure curve for the ventricle of the heart can thus create additional benefits from data already obtained by sensors that have previously been implanted for use in these other methods. Thus, the method of estimating the pressure curve need not necessarily include implanting a motion sensor specifically for use in the method. However, in some examples the present method may include a step of implanting the motion sensor, for example via techniques as described in the prior art referenced above.

The motion sensor may be placed at the heart in any location that enables measurement of heart movement so as to allow accurate determination of the timing of heart valve events. Thus, the sensor may be implanted within the tissue of the heart or in contact with the tissue of the heart, such as being implanted in the myocardium or attached to the surface of the myocardium. The sensor may alternatively be implanted in body tissue adjacent to the heart or at a medical device implanted adjacent to the heart. As discussed in WO 2014/207225 it is possible to use a motion sensor near to the heart, such as in a cardiac assist device, in order to monitor the heart. The location of the motion sensor can be flexible provided that it is implanted close enough to the heart to provide a clear indication of the timing of heart valve events. Multiple implanted sensors may be used in some cases, although this is not required.

In addition to obtaining the estimated pressure-time curve in the form of the scaled reference pressure-time curve the method may also include obtaining estimated pressure-motion data utilizing the estimated pressure-time curve. For example, this may be to obtain an estimated pressure-strain, pressure-displacement, or pressure-volume loop utilizing the estimated pressure-time curve. As will be appreciated by one skilled in the art an indication of the relationship between the pressure in the ventricle and the movement of the heart, including volume, strain, displacement, rotation, wall thickness, diameter and so on, can be invaluable in assessing the heart function. An estimate of the pressure-motion relationship can be obtained from the estimated pressure-time curve and suitable measurements of the motion of the heart, such as a global measure of heart motion like volume of the heart, a regional or local measure of the heart motion such as a strain at a point of interest, or any other measure of the heart motion such as a displacement, rotation or wall thickness. Conveniently, a displacement of the heart may be measured via a motion sensor and this may be the same motion sensor as is used to determine the timing of heart valve events.

Thus, the method may therefore be a method of obtaining an estimated pressure curve in the form of an estimated ventricular pressure-motion curve, which may be a pressure-motion loop. This estimated ventricular pressure-motion curve will correspond closely to the actual pressure-motion curve for the heart in the same way as was found by Russell et al. As noted above, obtaining an accurate estimated ventricular pressure-motion loop such as a pressure-strain loop has particular advantages since the area of the ventricular pressure-motion loop can be used to detect ischemia in real time as discussed by Halvorsen et al. The method may include calculating the area of an estimated left ventricular pressure-motion loop, such as a pressure-strain loop and providing an indication of a possible ischemia if the area drops below a threshold value.

The method may be carried out in real time with the estimated pressure-time curve and optionally the estimated pressure-motion loop being continually updated based on newly timing of the heart valve events and if available data for the peak systolic pressure.

The estimated pressure-motion curve may be obtained from the estimated pressure-time curve by combining the estimated pressure-time curve with appropriate volume, strain, wall thickness, rotation or displacement data. Advantageously, suitable data can be obtained from a motion sensor placed at the heart as noted above. Thus, a motion sensor implanted within the tissue of the heart, at the surface of the heart, or in adjacent tissue, may be used both to determine the timing of heart valve events as well as to measure movement of the heart, and the measurements from such a motion sensor may be used in determining the estimated pressure-time curve as well as obtaining the estimated pressure-motion loop from the estimated pressure-time curve.

A motion sensor can detect the heart valve events due to vibrations created by the heart valve events in the same way that a stethoscope can be used to hear such heart valve events. The heart valve events may include mitral valve events and/or aortic valve events. The heart valve events may include opening of a heart valve and/or closing of a heart valve. Thus, the heart valve events of the left ventricle may include some or all of mitral valve opening, mitral valve closing, aortic valve opening and/or aortic valve closing. Similarly, the valve events of the right ventricle may include some or all of tricuspid valve opening, tricuspid valve closing, pulmonary valve opening and/or pulmonary valve closing. In some examples the method includes determining the timing of all four of these heart valve events using data from the motion sensor.

The method includes scaling the reference curve along the time axis to fit it to the measured timing of the heart valve events to obtain the estimated pressure-time curve. Preferably this is done by scaling time axis for each of a plurality of intervals between consecutive heart valve events. Thus, the scaling of the time axis is not necessarily constant along the entirety of the time axis but may vary for different intervals between the heart valve events. In an example where the method determines the timing for all four of mitral valve opening, mitral valve closing, aortic valve opening and aortic valve closing then the scaling may be for a first interval between mitral valve closing and aortic valve opening, a second interval between aortic valve opening and aortic valve closing, a third interval between aortic valve closing and mitral valve opening, and a fourth interval between mitral valve opening and mitral valve closing. It will be appreciated that if only one cardiac cycle is involved then one of these intervals will complete a loop between the end of the cardiac cycle and the beginning of the same cardiac cycle. Alternatively, the method may used multiple cardiac cycles in which case the scaling may use intervals between adjacent cycles and/or the method use multiple cardiac cycles with the last cycle used in a loop with the first cycle. The method may use multiple cardiac cycles in order to find an averaged estimated pressure-time curve by scaling the reference pressure time curve against averaged and/or normalised timing for heart valve events over several cardiac cycles. The method may be carried out continuously in real-time in order to provide a real time estimated pressure curve for the ventricular pressure, and optionally to provide a real time estimated ventricular pressure-motion loop as discussed above.

The method may include an analysis of the time intervals between heart valve events. The relative size of these intervals and changes in the intervals may be used to draw conclusions about the condition of the patient.

The method does not need to use a peak pressure measurement as proposed by Russell et al., but in some examples the method may optionally include using blood pressure data to determine a value indicative of peak ventricular pressure and then scaling the reference pressure-time curve based on the determined peak pressure value. For example, the method may include determining a peak systolic pressure via blood pressure measurement such as a blood pressure cuff. In this case the reference pressure-time curve has a reference peak pressure and the method includes scaling the reference curve along the pressure axis to fit it with the determined value for peak pressure. Thus, the method may scale the reference curve with both pressure and time measurements. The method may include obtaining a peak systolic pressure measurement, for example via a non-invasive measurement such as a blood pressure cuff. This may be done continuously and/or in real-time in order to allow for continuous and/or real-time estimation of the pressure curve.

The reference pressure-time curve may be based on earlier measurements of the same patient or of one or more than one other patient(s). For example, the reference pressure-time curve may be generated by averaging and/or normalising multiple pressure-time curves measured from the patient(s) and determining averaged and/or normalised timing for the heart valve events. This may be done in a way similar to that described by Russell et al.

In example embodiments, the motion sensor is an accelerometer. Accelerometers are readily available with a sufficient level of accuracy and a required small size to be implanted at the heart. This could for example be a three-axis accelerometer for obtaining measurements of three dimensional heart movements, although other types of accelerometer may also be used. Suitable motion sensors also include MEMS tri-axis accelerometers and gyroscopes, for example. Suitable sensors are not limited to traditional motion sensors, but may also include sensors that may capture motion events using a physical effect other than that relied upon by, for example, an accelerator. A suitable sensor for certain embodiments may be a microphone that could be used to detect/listen for the valve events/sounds (similar to a stethoscope), and these valve sounds could be used to detect timing of the valve events. In particular, a microphone may potentially be equivalent to an accelerometer in the sense that they both detect vibrations. Furthermore, a combination of sensors may be used in embodiments of the present approach. For example, a combined accelerometer/gyroscope sensor, where an accelerometer (or a microphone) may be used to detect the valve events and the gyro may be used to measure rotation. More generally, in a combined sensor, one sensor may be used for the determination of pressure, while the second sensor may be used to measure motion to create the pressure-motion loop. In various embodiments, the sensors may include one or more of the following: accelerometer, gyroscope, microphone, ultrasound detector, electromagnetic tracking sensor, magnetometer and electromyogram.

Viewed from a second aspect, the invention provides a heart monitoring system comprising: a motion sensor for implantation at the heart to monitor motion of the heart; and a data processing apparatus arranged to: receive data from the motion sensor and use the data from the motion sensor to determine the timing of heart valve events; scale a reference pressure-time curve including timing of reference heart valve events in order to fit the reference pressure-time curve to the motion sensor data, the scaling comprising scaling the reference curve along the time axis to fit it to the measured timing of the heart valve events; and thereby obtain an estimated pressure-time curve in the form of the scaled reference pressure-time curve.

The data processing apparatus, which may be a computer device or the like, may hence be arranged to carry out the method of the first aspect based on data from the implantable motion sensor. The data processing apparatus may be arranged to carry out the method including any of the further steps and optional features discussed above.

The motion sensor may already be present at the heart and thus could have been implanted in a separate earlier procedure. The use of a motion sensor implanted at the heart has been proposed for various reasons as discussed above. Embodiments of the heart monitoring system include systems where the motion sensor is implanted in the body and a lead extends out of the body to provide data to the data processing apparatus. The system may also take the form of a kit of parts ready to be used with a patient and hence comprising an implantable motion sensor along with the data processing apparatus.

In example embodiments the motion sensor is an accelerometer as discussed above. As noted above and below, there are different types of events that are relevant to the scaling of the pressure-time curve, and for each type of event, more than one type of sensor may be used to measure each particular event. Given the relevance of the different types of events, and the applicability of the different sensors that may be used for each type of event, a "sensor," for example, includes more than a traditional "motion sensor" (e.g., an accelerometer) when seeking to capture a heart valve event.

In a further aspect, the invention provides a computer programme product comprising instructions that, when executed, will configure a data processing apparatus to perform the method of the first aspect and optionally the method including any of the further steps and optional features discussed above. Thus, the computer programme product may configure the data processing apparatus to: receive data from the motion sensor; use the data from the motion sensor to determine the timing of heart valve events; scale a reference pressure-time curve including timing of reference heart valve events in order to fit the reference pressure-time curve to the motion sensor data, the scaling comprising scaling the reference curve along the time axis to fit it to the measured timing of the heart valve events; and thereby obtain an estimated pressure-time curve in the form of the scaled reference pressure-time curve.

Certain preferred embodiments of the present invention will now be described in greater detail, by way of example only and with reference to the accompanying drawings, in which:

FIG. 1 shows an example left ventricular pressure-time curve along with heart valve opening and closing timing;

FIG. 2 shows the actual left ventricular pressure-time curve of FIG. 1 overlaid with a reference pressure-time curve as well as an estimated pressure-time curve obtained via scaling the reference pressure-time curve to fit measured peak systolic pressure and measured timing for heart valve opening and closing; and FIG. 3 shows how left ventricular pressure-displacement loops vary depending on the condition of the patient.

A method of determining an estimated pressure curve for the ventricle of the heart is described herein with the left ventricle being used by way of example. FIG. 1 shows an example of an actual pressure-time curve 12 for a left ventricle. As shown in this Figure the pressure-time curve 12 can be characterised by the maximum pressure (peak systolic pressure) as well as the timing of mitral valve opening, mitral valve closing, aortic valve opening and/or aortic valve closing.

In accordance with the proposed method for estimating the ventricular pressure the maximum pressure can optionally be measured (e.g. via blood pressure cuff) and the timing of the mitral valve opening (MVO), mitral valve closing (MVC), aortic valve opening (AVO) and/or aortic valve closing (AVC) can be determined by means of a motion sensor implanted at the heart. The motion sensor may for example be an accelerometer implanted at the heart as described in EP 1458290 or U.S. Pat. No. 8,282,568. The timing of the various heart valve events is determined based on the vibrations measured by the motion sensor. The motion sensor effectively detects the noises made as the heart valves open or close.

These measurements thus provide characteristic values of the left ventricular pressure curve as shown by the dashed horizontal and vertical lines in the plot of FIG. 1. The horizontal dashed line relates to the peak pressure (optional) and the four vertical dashed lines relate to the four heart valve opening and closing events. In between the four vertical dashed lines are time intervals that are characteristic of the cycle of the heart that has been measured. These characteristic values are used in order to obtain an estimated pressure-time curve by scaling a reference pressure-time curve 14 as shown in FIG. 2.

The reference pressure-time curve 14 is obtained from earlier measurements of the patient of interest or from measurements of one or more similar patient(s). The reference curve 14 includes timing of reference heart valve events and a reference peak systolic pressure. Preferably it is based on an average of measurements of several different cardiac cycles. The method for obtaining the reference curve 14 may be similar to that described by Russell et al.

FIG. 2 shows an example reference pressure-time curve 14 in a dashed grey line 14 overlaid above the measured pressure-time curve 12 of FIG. 1. The size of the reference curve 14 is exaggerated for clarity. The reference curve 14 is scaled to fit with the heart valve timing events and can optionally be scaled to fit it with the measured peak systolic pressure. If the peak pressure is not measured, then the reference curve can be used as a normalised curve in terms of absolute pressure with the scaling relating only to the measured timing of the heart valve events. The optional scaling along the pressure axis applies the same multiplication factor for the whole axis to fit the peak systolic pressure of the reference curve with the measured peak systolic pressure. The scaling along the time axis is done by scaling time axis for each of the intervals between consecutive heart valve events, i.e. for a first interval between mitral valve closing and aortic valve opening, a second interval between aortic valve opening and aortic valve closing, a third interval between aortic valve closing and mitral valve opening, and a fourth interval between mitral valve opening and mitral valve closing. Thus, the scaling of the reference curve 14 along the time axis is not necessarily constant along the entirety of the time axis but may vary for different intervals between the heart valve events. The result of the scaling is an estimated pressure-time curve 16 as shown by the solid grey line 16 in FIG. 2. This closely corresponds to the actual pressure-time curve 12, as shown by the black line 16.

The method uses data from a motion sensor that has been implanted at the heart. The motion sensor may be placed in any location that enables measurement of heart movement so as to allow accurate determination of the timing of heart valve events. Thus, the sensor may be implanted within the tissue of the heart or in contact with the tissue of the heart, such as being implanted in the myocardium or attached to the surface of the myocardium. The implanted sensor can be as described in WO 2014/207225, EP 1458290 or U.S. Pat. No. 8,282,568. The location of the motion sensor is flexible provided that it is implanted close enough to the heart to provide a clear indication of the timing of heart valve events, although in some examples the sensor is also close enough to the heart to measure movements of the heart in order to determine heart displacement/strain, as discussed below. Multiple implanted sensors may be used in some cases, although this is not required.

Once the estimated pressure-time curve 16 has been obtained by scaling the reference pressure-time curve 14, then an estimated pressure-motion loop is obtained from the estimated pressure-time curve 16 by combining the estimated pressure-time curve 16 with appropriate volume, strain, wall thickness, rotation or displacement data. Suitable displacement data can be obtained from a motion sensor placed at the heart, such as a motion sensor implanted in the myocardium or at the surface of the myocardium. This estimated left ventricular pressure-motion loop will correspond closely to the actual pressure-motion loop for the heart. The area of the left ventricular pressure-motion loop varies depending on the condition of the patient as shown in FIG. 3 with reference to a pressure-displacement loop. This can be used to detect ischemia in real time as discussed by Halvorsen et al. The area of the estimated left ventricular pressure-motion loop can therefore be calculated with an indication of a possible ischemia being provided if the area drops below a threshold value. This can be carried out in real time with the estimated pressure-time curve and the estimated pressure-motion loop being continually updated based on newly obtained data for the (optional) peak systolic pressure and the timing of the heart valve events.

The data from the motion sensor along with the other data used in the methods described herein, such as peak systolic pressure, can be automatically processed in line with the method described above by a data processing apparatus such as a computer or similar. Thus, the method can be implemented via a data processing apparatus that receives and processes the data. This may be a part of a broader heart monitoring system that also includes controls and/or a display for receiving inputs from a user and providing outputs to the user. The output of the data processing apparatus may be a plot of the estimated pressure-time curve and/or a plot of the estimated pressure-motion loop and these can be shown on the display. The area of the estimated pressure-motion loop may also be displayed, along with an indication of any potential problems such as ischemia.

The motion sensor can be an accelerometer such as a three-axis accelerometer. This can be used for obtaining measurements of three dimensional heart movements as well as detecting the vibrations resulting from heart valve opening and closing.

In various embodiments, events may include events other than valve events. While the above discussion focusses on valve events to be the time markers to scale the pressure curve along the time-axis, there may be other time events during the cardiac cycle which can be detected consistently and used as time-markers. For example, the early filling phase which creates the maximum velocity of some regions of the ventricular wall during the cardiac cycle, may serve as a distinct time-marker which may be equally good to use in the present approach. As noted above, for each event of interest, embodiments include types of sensor that may capture the particular event. Thus, for example, a heart movement event may be captured by an accelerometer, or by a microphone, or other device that may detect this event.

The invention claimed is:

1. A method of determining an estimated pressure-time curve for a ventricle of a heart, the method comprising:
    receiving data from a sensor that has been implanted at the heart;
    determining timing of heart cycle events based on the received data;
    scaling a reference pressure-time curve using the determined timing of heart cycle events in order to fit the reference pressure-time curve to the received data, the scaling comprising scaling the reference pressure-time curve along a time axis to fit to the determined timing of the heart cycle events; and
    determining the estimated pressure-time curve based on the scaled reference pressure-time curve.

2. The method of claim 1, wherein the determining the estimated pressure-time curve is performed separate to a step of implanting the sensor at the heart.

3. The method of claim 1, further comprising:
    deriving an estimated pressure-motion curve from the estimated pressure-time curve using at least one of the received data or data from a motion sensor.

4. The method of claim 3, further comprising:
    obtaining an estimated pressure-motion loop; and
    calculating an area of the estimated pressure-motion loop.

5. The method of claim 4, wherein the obtaining the estimated pressure-motion loop includes using the estimated pressure-time curve by combining the estimated pressure-time curve with heart motion data obtained from the implanted sensor.

6. The method of claim 1, wherein the determining the estimated pressure-time curve is carried out in real time with the estimated pressure-time curve being continually updated based on newly obtained data for the timing of the heart cycle events.

7. The method of claim 1, wherein the heart cycle events include at least one of mitral valve opening, mitral valve closing, aortic valve opening and/or aortic valve closing.

8. The method of claim 1, wherein the scaling the reference pressure-time curve along the time axis to fit to the measured timing of the heart cycle events to obtain the estimated pressure-time curve is done by scaling the time axis for each of a plurality of intervals between consecutive heart cycle events.

9. The method of claim 1, wherein the reference pressure-time curve is based on earlier measurements of the same patient or of one or more than one other patients.

10. The method of claim 1, further comprising:
    scaling the reference pressure-time curve using the determined timing of heart cycle events without any use of peak pressure to scale the reference pressure-time curve.

11. The method of claim 1, further comprising:
    using blood pressure data to determine a value indicative of peak ventricular pressure; and
    scaling the reference pressure-time curve along a pressure axis based on the determined peak pressure value.

12. The method of claim 1, wherein the implanted sensor is an accelerometer.

13. The method of claim 1, further comprising:
    implanting the sensor at the heart.

14. A heart monitoring system comprising:
    a motion sensor for implantation at a heart to monitor motion of the heart; and
    a data processing apparatus arranged to:
    receive data from the motion sensor and use the data from the motion sensor or a dedicated sensor for determining timing of heart cycle events;
    scale a reference pressure-time curve including timing of reference heart cycle events in order to fit the reference pressure-time curve to the data from the motion sensor, the scaling comprising scaling the reference pressure-time curve along a time axis to fit to the measured timing of the heart cycle events; and
    obtain an estimated pressure-time curve in a form of the scaled reference pressure-time curve.

15. The heart monitoring system of claim 14, wherein the motion sensor is implanted at the heart and the data processing apparatus is coupled to the motion sensor to receive data in real-time.

16. A non-transitory computer-readable storage medium comprising instructions that, when executed, will configure a data processing apparatus to perform:
    receiving data from a sensor that has been implanted at a heart;
    determining timing of heart cycle events based on the received data;
    scaling a reference pressure-time curve using the determined timing of heart cycle events in order to fit the reference pressure-time curve to the received data, the scaling comprising scaling the reference pressure-time curve along a time axis to fit to the determined timing of the heart cycle events; and determining the estimated pressure-time curve based on the scaled reference pressure-time curve.

* * * * *